US012718441B2

(12) United States Patent
Koehler

(10) Patent No.: US 12,718,441 B2
(45) Date of Patent: Aug. 25, 2026

(54) METHOD FOR USE IN CT RECONSTRUCTION

(71) Applicant: KONINKLIJKE PHILIPS N.V., Eindhoven (NL)

(72) Inventor: Thomas Koehler, Norderstedt (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 396 days.

(21) Appl. No.: 18/282,059

(22) PCT Filed: Mar. 2, 2022

(86) PCT No.: PCT/EP2022/055274
§ 371 (c)(1),
(2) Date: Sep. 14, 2023

(87) PCT Pub. No.: WO2022/194555
PCT Pub. Date: Sep. 22, 2022

(65) Prior Publication Data
US 2024/0153160 A1 May 9, 2024

(30) Foreign Application Priority Data
Mar. 15, 2021 (EP) .................................... 21162625

(51) Int. Cl.
*G06T 12/10* (2026.01)
*A61B 6/03* (2006.01)
*A61B 6/40* (2024.01)

(52) U.S. Cl.
CPC .............. *G06T 12/10* (2026.01); *A61B 6/032* (2013.01); *A61B 6/4085* (2013.01); *G06T 2207/10081* (2013.01); *G06T 2211/40* (2013.01)

(58) Field of Classification Search
CPC ....... A61B 6/032; A61B 6/4085; A61B 6/027; A61B 6/4021; A61B 6/4028;
(Continued)

(56) References Cited

U.S. PATENT DOCUMENTS 5,960,056 A * 9/1999 Lai ........................ A61B 6/027
378/4
6,115,445 A * 9/2000 Lai ........................ A61B 6/032
378/4
(Continued)

FOREIGN PATENT DOCUMENTS

WO WO2007026273 A2 3/2007

OTHER PUBLICATIONS

PCT International Search Report, International application No. PCT/EP2022/055274, Jul. 19, 2022.
(Continued)

*Primary Examiner* — Irakli Kiknadze
(74) *Attorney, Agent, or Firm* — Larry Liberchuk

(57) ABSTRACT

A method of preprocessing cone beam projection data acquired using a dual x-ray focal spot acquisition approach in which projection data is acquired over a series of angular positions of the CT scanner about a body, and wherein at least two angularly displaced x-ray sources (focal spots) are alternately activated as the scanner rotates orbitally around the body. The pre-processing involves a resampling of the projection data from the first and second focal spots to a new virtual sampling point part way between the first and second focal spots.

10 Claims, 9 Drawing Sheets

(58) Field of Classification Search
CPC ... A61B 6/4275; A61B 6/4441; G06T 11/005; G06T 2211/432; G06T 2211/40; G06T 2207/10081; G06T 17/00; G06T 11/006; G06T 12/10; G06T 12/00; G06T 11/003; G06T 2211/416; G06T 12/20; G01N 23/046; G01N 2223/419; G01N 2223/416; G01N 2223/501; G01T 1/2985; H05G 1/52; H01J 2235/068; Y10S 378/901
USPC .................................................. 378/4, 19, 62
See application file for complete search history.

(56) References Cited

U.S. PATENT DOCUMENTS

| | | | | |
|---|---|---|---|---|
| 6,118,841 | A * | 9/2000 | Lai | A61B 6/032 378/19 |
| 2008/0304727 | A1 * | 12/2008 | Doyle | G01R 33/561 382/131 |
| 2013/0094742 | A1 * | 4/2013 | Feilkas | A61B 6/584 382/131 |

OTHER PUBLICATIONS

Wang X. et al., “Physics-Based Iterative Reconstruction for Dual Source and Flying Focal Spot Computed Tomography”, arxiv.org, Cornell University Library, 201 Olin Library Cornell University Ithaca, NY 14853, Nov. 15, 2020 (Nov. 15, 2020), XP081813726.
Kachelriess M. et al., “Flying Focal Spot (FFS) in Cone-Beam CT”, IEEE Transactions on Nuclear Science, vol. 53, No. 3, Jun. 1, 2006 (Jun. 1, 2006), pp. 1238-1247, XP055114678.
Forthmann P. et al., “Penalized Maximum-Likelihood Sinogram Restoration for Dual Focal Spot Computed Tomography”, Physics in Medicine and Biology, Jan. 1, 2007 (Jan. 1, 2007), pp. 4513-4523, XP055832361.
Heuscher D. et al., “Redundant Data and Exact Helical Cone-Beam Reconstruction”, Redundant data in helical CB CT, Physics in Medicine and Biology, Institute of Physics Publishing, Bristol GB, vol. 49, No. 11, Jun. 7, 2004 (Jun. 7, 2004), pp. 2219-2238, XP020023728.
Defrise M. et al., “A Cone-Beam Reconstruction Algorithm Using Shift-Variant Filtering and Cone-Beam Backprojection”, IEEE Transaction on Medical Imaging, vol. 13, No. 1, Mar. 1994.

* cited by examiner (a) (b) (c)

(a) (b) (c)

METHOD FOR USE IN CT RECONSTRUCTION

FIELD OF THE INVENTION

This invention relates to a method for use in x-ray computed tomography image reconstruction, in particular cone beam x-ray CT image reconstruction.

BACKGROUND OF THE INVENTION

A conventional computed tomography (CT) scanner includes an x-ray radiation generator mounted on a rotatable gantry opposite one or more integrating detectors. The x-ray generator rotates around an examination region located between the x-ray generator and the one or more detectors and emits (typically polychromatic) radiation that traverses the examination region and a subject and/or object disposed in the examination region. The one or more detectors detect radiation that traverses the examination region and generate a signal (or projection data) indicative of the examination region and the subject and/or object disposed therein. The projection data refers to the raw detector data.

A reconstructor is typically further used to process the projection data and reconstruct a volumetric image of the subject or object. The volumetric image is composed of a plurality of cross-sectional image slices which are each generated from the projection data through a process of tomographic reconstruction, such as through application of a filtered back projection algorithm. The reconstructed image data is effectively an inverse radon transform of the raw projection data.

There is a renewed interest in the CT field to build systems with very large coverage, e.g. coverage in the range of 16 cm. Two major clinical applications that would benefit from such a system are axial cardiac CT and brain perfusion without the need to move the patient back and forth.

An axial scan means a scan in which a subject remains stationary within the scanning region surrounded by the rotatable gantry, and the gantry rotates orbitally around the stationary patient. An axial 'full scan' means a scan in which data is acquired over a full 360 degree rotation of the x-ray source around the body being scanned. An axial 'short scan' means a scan in which data is acquired for less than a full 360 degree rotation of the x-ray source. A short scan may often be used for applications where motion artefacts could be an issue, for example when imaging organs which undergo movement such as the heart or the lungs, or other objects which are moved as a result of the organs, for example the liver.

To improve resolution of acquired CT images, one common mode of CT scanning employs use of a cone beam x-ray source and a 2D detector array. A cone beam x-ray source generates an x-ray beam which effectively has a rectangular cross-section, i.e. the beam has a fan angle in an x and y direction. It is used in combination with an x-ray detector which comprises multiple rows (a 2D array). The use of a cone beam geometry leads to a more complex method of reconstruction of the resulting projection data.

A common difficulty in cone beam CT is meeting the so-called data sufficiency condition (DSC), failure of which may lead to cone beam artefacts in reconstructed images. In particular, even a full-scan axial acquisition does not provide sufficient data for exact reconstruction. This is known as the missing data problem in axial CT. The root cause of the missing data problem is the fact that data acquisition by a cone-shaped x-ray beam along a circular source trajectory cannot cover every data point in a 3D object region about which the source trajectory travels.

The missing data problem can be understood by considering acquisition planes in Radon space. All reconstruction techniques involve at least one effective inverse radon transformation of acquired measurement data. In particular, the 3D object to be reconstructed can be represented by an object function, $f(r)$ ($r=(\varphi, \theta, r)$ in a spherical coordinate system. The 3D x-ray transform of $f(r)$ is defined as the integral along line L:

$$Xf(r) = \int_L f(r)dr = \int_{-\infty}^{\infty} f(r_0 + lk)dl$$

where $r_0$ denotes the vector connecting a point in line L and the origin of a coordinate system, and k is the unit vector with its direction parallel to that of line L.

The radon transform of a 3D object function can be defined as:

$$Rf(r) = \int_{\varphi=0}^{2\pi} \int_{\theta=-\pi/2}^{\pi/2} \int_{\rho=0}^{\infty} f(r)\delta(r \cdot n - \rho)\rho\cos\theta d\rho d\theta d\varphi$$

The Radon transform of a 3D object function is an integral on the plane that is jointly determined by the norm, n, and distance ρ from the origin, O, and such a plane is called the radon plane, with its norm defined, in spherical co-ordinates, as:

$$n = (\sin\theta\cos\varphi, \sin\theta\sin\phi, \cos\theta)$$

FIG. 1 schematically depicts the acquisition of data corresponding to a Radon plane 12 (a surface in Radon space), based on measurement data across a 2D detector array 14.

Theoretically, if all the information in the Radon domain is known, the 3D object function f(r) can be reconstructed from $Rf(r)$ using a 3D inverse radon transform. The skilled person will be aware of formulations for the inverse Radon transform.

Thus, from the point of view of Radon space, as a cone beam scanner rotates orbitally around the 3D object, it acquires data in a torus-shaped volume of Radon planes. This is illustrated in FIG. 2(*a*) for an acquisition where the source rotates in the xy plane at z=0.

It can be seen that even with an entire 360° rotation around the object, there is still a region of missing data near the z-axis in Radon space (known mathematically as a null space). In the full rotation scan, shown in FIG. 2(*a*), there is a cone shaped null space near the z-axis.

In an axial scan with 180° rotation, missing data are located in a wedge-shaped region, as illustrated in FIG. 2(*b*). FIG. 2(*c*) shows the acquired Radon planes for axial short scan (180° plus the fan angle). There is again a wedge of missing data, this time closed (only) in the xy plane.

In each of the cases, in addition to missing data there are also redundant data (i.e. locations in the Radon domain where the Radon planes overlap or intersect).

Algorithms have been developed to enable reconstruction of 3D images in a stable way based on the incomplete data. One widely used algorithm for circular orbits is the Feldkamp, Davis and Kress (FDK) algorithm (L. A. Feldkamp, L. C. Davis, and J. W. Kress, "Practical cone-beam algorithm", J. Opt. Soc. Am. 1, pp. 612-619, 1984). This is a fairly simple extension of the usual 2D filtered back-projection for fan beam data to the 3D domain (to accommodate cone beam projections).

For a full scan axial acquisition, two redundant measurements are acquired for each point in Radon space that is measured. This homogeneous sampling makes proper reconstruction relatively easy using the FDK algorithm.

However, for axial short scan reconstruction (e.g. for cardiac CT imaging), the Radon-space contains a greater quantity of unmeasured areas and at the same time, the area of redundantly measured data differs from the area of measured data. Thus, a dedicated redundancy compensation algorithm needs to be applied. It is the current standard in medical CT to rebin the data which are natively acquired in cone-beam geometry using a cylindrical detector into the so-called wedge geometry (wedge rebinning) Rebinning refers to a process of resampling data to a different, more convenient, geometry. Wedge rebinning is the 3D analog of parallel beam rebinning in 2D. Redundancy weighting is performed by heuristically adapting the known overscan method from 2D CT to 3D CT. An example of a wedge rebinning algorithm is outlined in detail in the document U.S. Pat. No. 6,104,775A.

However, wedge rebinning leads to only an approximate reconstruction, with artefacts still occurring in the resulting image data.

There are also methods known in the field that can utilize all measured data correctly, i.e. which can perform an exact reconstruction, with fully accurate redundancy weighting. This algorithm can be applied to any acquisition geometry, including axial full scan, axial short scan, and helical scan. The shift-variant filtering method proposed by Defrise and Clack, is one such method, and is outlined in this paper: Defrise and Clack, IEEE Transaction on Medical Imaging, 13(1), 1994. The method was further developed by Schomberg in the paper: H. Schomberg, Proceedings of the Fully 3D conference 2005, Salt Lake City, page 184. This is known as the Defrise-Clack-Schomberg (DCS) method.

Another example reconstruction algorithm which follows the same principles is also detailed in the following paper by Kudo and Saito: "Derivation and implementation of a cone-beam reconstruction algorithm for nonplanar orbits", IEEE Trans Med Imaging, 1994; 13(1):196-211.

FIG. 3 shows image reconstruction results of a 16 cm CT scanner using different scan and reconstruction approaches. FIG. 3(*a*) shows the reconstruction result applying the wedge reconstruction method to projection data acquired with an axial short scan. FIG. 3(*b*) shows the reconstruction result applying a frequency split wedge reconstruction method to projection data acquired with an axial full scan, and FIG. 3(*c*) shows the reconstruction result applying the Defrise-Clack-Schomberg (DCS) method to projection data acquired with an axial short scan. The frequency split wedge reconstruction method is described for example in the document WO2020193546.

It can be seen that the DCS method generates far fewer artefacts than the short scan wedge reconstruction method (which creates artefacts due to missing data and due to improper weighting of redundant data) and fewer artefacts still than the frequency split method, the latter of which requires a full scan axial acquisition. The remaining artefacts in the DCS image reconstruction are solely due to missing data.

In state of the art medical CT systems, dual-focal spot (DFS) acquisition is commonly used to increase spatial resolution and reduce aliasing. In dual focal spot acquisition, the location of the x-ray tube focal spot (i.e. the x-ray source location) is alternated at high frequency between two adjacent positions throughout the orbital rotation of the CT scanner about the examination region. In effect, two datasets are acquired concurrently as the x-ray scanning apparatus rotates about the 3D object, one corresponding to the first focal spot, and one corresponding to the second focal spot.

The dual focal spot (DFS) acquisition approach is described in detail in the document U.S. Pat. No. 4,637,040, and the reader is referred to this paper for implementation details of the dual focal spot CT acquisition method. The dual focal spot projection data can be reconstructed using a wedge reconstruction algorithm. The dual datasets corresponding to the two different focal spots (two different x-ray source locations) can be handled in the wedge reconstruction algorithm as part of the parallel rebinning (resampling) operation in which the projection data for each cone-beam projection is re-binned into a set of effective parallel beam measurement samples.

However, for the more sophisticated algorithm by Defrise, Clack, and Schomberg, or Kudo and Saito, the parallel rebinning does not take place, and instead all data are processed in the cone beam geometry.

Thus, the effective interleaving of the projection data from the two focal spots which is inherently achieved in wedge rebinning is not feasible within these reconstruction methods. As a result, these methods currently cannot be used for data acquired using the dual focal spot acquisition approach. Thus, the range of reconstruction methods available for use with dual focal spot projection data is limited.

There is need for a means of enabling a broader range of image reconstruction methods to be applied to projection data acquired using the dual focal spot approach.

SUMMARY OF THE INVENTION

The invention is defined by the claims.

According to examples in accordance with an aspect of the invention, there is provided a method for use in reconstruction of cone beam x-ray computed tomography (CT) projection data, comprising:

- receiving input cone beam CT projection data of a body, wherein the CT projection data comprises at least first and second x-ray detector measurement data, corresponding to respective measurement data acquired with an x-ray generator providing alternately activated first and second x-ray point sources displaced relative to one another along a direction of an orbital rotational axis of the generator about the body, and the x-ray sources generating respective x-ray cone beams, and wherein each of the first and second measurement data comprises measurement data for a series of orbital angular positions of the generator about the body;
- processing the first and second measurement data with a re-sampling operation to derive a third set of measurement data corresponding to a virtual single x-ray point source located part way between the first and second x-ray point sources, the third set of measurement data based on a combination of the first and second measurement data;
- applying a reconstruction algorithm to the third set of measurement data. This thereby results in reconstructed image data.

The third set of measurement data may represent projection data for a single virtual cone beam propagated from said virtual single x-ray point source.

The third set of measurement data may represent projection data for a plurality of orbital angular sampling positions of said virtual single x-ray point source about the body.

Embodiments of the present invention are based on the concept of performing an angular re-sampling of the data from the two x-ray focal spots (x-ray point sources) to a common angular grid. In other words, the data are re-binned to a new dataset which represents virtual projection data from a virtual single source point located in-between the first and second x-ray source points, this single source point having a plurality of orbital angular sampling positions. Once the data are mapped to a single common set of angular sampling points, they are effectively interleaved to generate cone-beam projections with an increased number of effective detector pixels. In other words, the two sets of measurement data are mapped to a single set of orbital angular sampling bins, where this set of angular sampling bins is twice the number of angular sampling bins (detector columns) as provided by each of the two measurement data sets alone.

Optionally, the reconstruction algorithm may include a data redundancy compensation operation applied to the third set of measurement data. This may be a pre-determined operation, or it may be determined in real time during execution of the reconstruction algorithm.

These interleaved projections are then suitable for application of a broad range of reconstruction algorithms, including the DCS reconstruction algorithm discussed above.

The first and second x-ray point sources are displaced relative to one another within a reference frame of the x-ray generator, i.e. they are displaced relative to one another on or in the x-ray generator. Their displacement is preferably a displacement along the direction of the orbital axis of the gantry. Thus the generator carries an x-ray generating arrangement operable to generate two point sources displaced relative to one another, and wherein the orbital rotation of the generator moves each of these point sources around a series of orbital angular positions to acquire the first and second measurement data.

The first measurement data corresponds to data for the first x-ray point source, and the second measurement data corresponds to data for the second x-ray point source.

The virtual single x-ray point source is at a point part way spatially between the first and second point sources. The third measurement data comprises virtual measurement data for a series of virtual point source locations part way between each pair of the first and second x-ray point source locations at the different orbital angular positions of the generator.

The x-ray generator may comprise at least one x-ray tube.

The reconstruction algorithm may be a reconstruction algorithm which does not perform parallel or wedge rebinning of data. The reconstruction algorithm may be an algorithm which performs no rebinning. The reconstruction algorithm may be an algorithm which processes the projection data in the cone-beam geometry, i.e. which retains the data in the cone beam geometry throughout the reconstruction algorithm. Embodiments of the invention find particularly advantageous application for such reconstruction algorithms, since these algorithms, by not rebinning data in these ways, do not themselves inherently perform any interleaving or amalgamation of the acquired data to a common set of angular sampling points.

The received CT projection data may be projection data for an axial scan. This means for example a CT scan in which the x-ray generator is rotated about the scanned body in the examination region, and in which the body is not moved axially through the examination region (through the gantry). The received CT projection data may be projection data for an axial scan in which the x-ray generator is rotated through a series of orbital positions covering an angular range of less than 360 degrees (about the scanned body). Embodiments of the invention find particularly advantageous application for such reconstruction algorithms, since reconstruction of such projection data is inherently more prone to artefacts caused by the missing data problem.

The deriving of the third set of measurement data may be based on interpolation between the first and second sets of measurement data. The interpolation results in a new set of virtual measurement data comprising virtual detector readings for a virtual x-ray cone beam projected from the virtual single x-ray point source, based on interpolation between the detector readings for the first and second x-ray source points.

In accordance with one or more embodiments, the virtual single point source location may be a mid-point between the first and second x-ray point source locations, along the orbital rotational axis.

Use of the midpoint is preferred since this means that the interpolation weights used to resample the data from each of the first and second x-ray source points is the same, meaning that the interpolation induced smoothing is the same for both source points, minimizing the risk of artefacts.

In one or more embodiments, the interpolation may be angular interpolation along said orbital rotational axis about the body.

In one or more embodiments, the third set of measurement data may comprise, for each orbital angular sampling position of the single virtual point source, twice the number of detector angular sampling bins as for each of the first and second sets of measurement data.

In one or more embodiments, the virtual single cone beam projection may comprise an interleaving of the first and second cone beam projections.

In one or more embodiments, the re-sampling may comprise an effective rotation of each of the first and second cone beams about an isocentre of the orbital rotation such that their point sources coincide at said single virtual point source location.

Examples in accordance with a further aspect of the invention provide a computer program product comprising code means configured, when executed on a processor, to cause the processor to perform a method in accordance with any example or embodiment outlined above or described below, or in accordance with any claim of this application.

Examples in accordance with a further aspect of the invention provide a processing arrangement for use in reconstruction of cone beam x-ray computed tomography (CT) projection data, comprising: an input/output; and one or more processors. The one or more processors are adapted to:

receive, at the input/output, input cone beam CT projection data of a body, wherein the CT projection data comprises at least first and second x-ray detector measurement data, corresponding to measurement data acquired with an x-ray generator providing alternately activated first and second x-ray point sources displaced relative to one another along an orbital rotational axis of the generator about the body, and the x-ray sources generating respective x-ray cone beams, and wherein each of the first and second measurement data comprises measurement data for a series of orbital angular positions of the generator about the body;

process the first and second measurement data with a re-sampling operation to derive a third set of measurement data corresponding to a virtual single x-ray point source located part way between the first and second x-ray point sources, the third set of measurement data based on the first and second measurement data;

apply a reconstruction algorithm to the third set of measurement data.

Optionally, the reconstruction algorithm may include a data redundancy compensation operation applied to the third set of measurement data. This may be a pre-determined operation, or it may be determined in real time during execution of the reconstruction algorithm.

Examples in accordance with a further aspect of the invention provide an x-ray computed tomography (CT) imaging system, comprising:

an x-ray CT imaging apparatus, comprising an x-ray generator and an x-ray detector, the x-ray detector and x-ray generator mounted on a rotatable gantry permitting orbital angular rotation of the detector and generator around the examination region, wherein the x-ray generator is adapted in use to alternately activate first and second x-ray point sources displaced relative to one another along the orbital rotational axis of the generator, and the first and second x-ray sources generating respective x-ray cone beams, and wherein the x-ray detector comprises a 2D detector array.

The system further comprises a processing module adapted to:

obtain from the x-ray detector first and second x-ray detector measurement data, corresponding to measurement data acquired with the alternately activated first and second x-ray point sources, and the first and second measurement data each comprising measurement data for a series of orbital rotational positions of the generator about the body;

process the first and second measurement data with a re-sampling operation to derive a third set of measurement data corresponding to a virtual single x-ray point source located part way between the first and second x-ray point sources, the third set of measurement data based on the first and second measurement data;

apply a reconstruction algorithm to the third set of measurement data.

Optionally, the reconstruction algorithm may include a data redundancy compensation operation applied to the third set of measurement data. This may be a pre-determined operation, or it may be determined in real time during execution of the reconstruction algorithm.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figures 1, 2, 3:
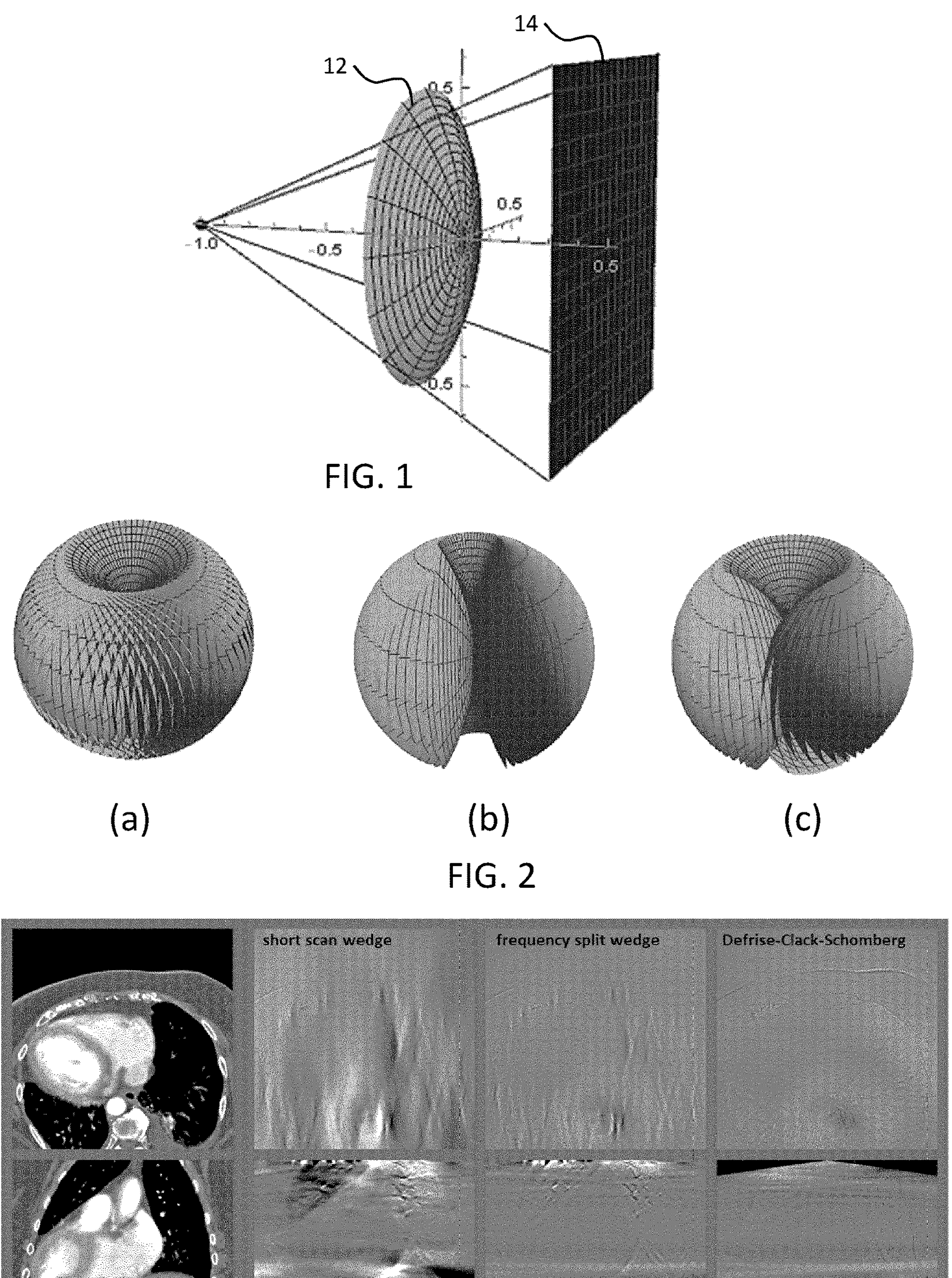
FIG. 1 schematically illustrates a projection data sample in the radon domain.
FIG. 2 schematically illustrates the missing data problem in cone beam CT image reconstruction.
FIG. 3 illustrates example image reconstruction results using different prior art reconstruction methods.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a method of preprocessing cone beam projection data acquired using a dual x-ray focal spot acquisition approach in which projection data is acquired over a series of angular positions of the CT scanner about a body, and wherein at least two angularly displaced x-ray sources (focal spots) are alternately activated as the scanner rotates orbitally around the body. The pre-processing involves a resampling of the projection data from the first and second focal spots to a new virtual sampling point part way between the first and second focal spots.

Figure 4:
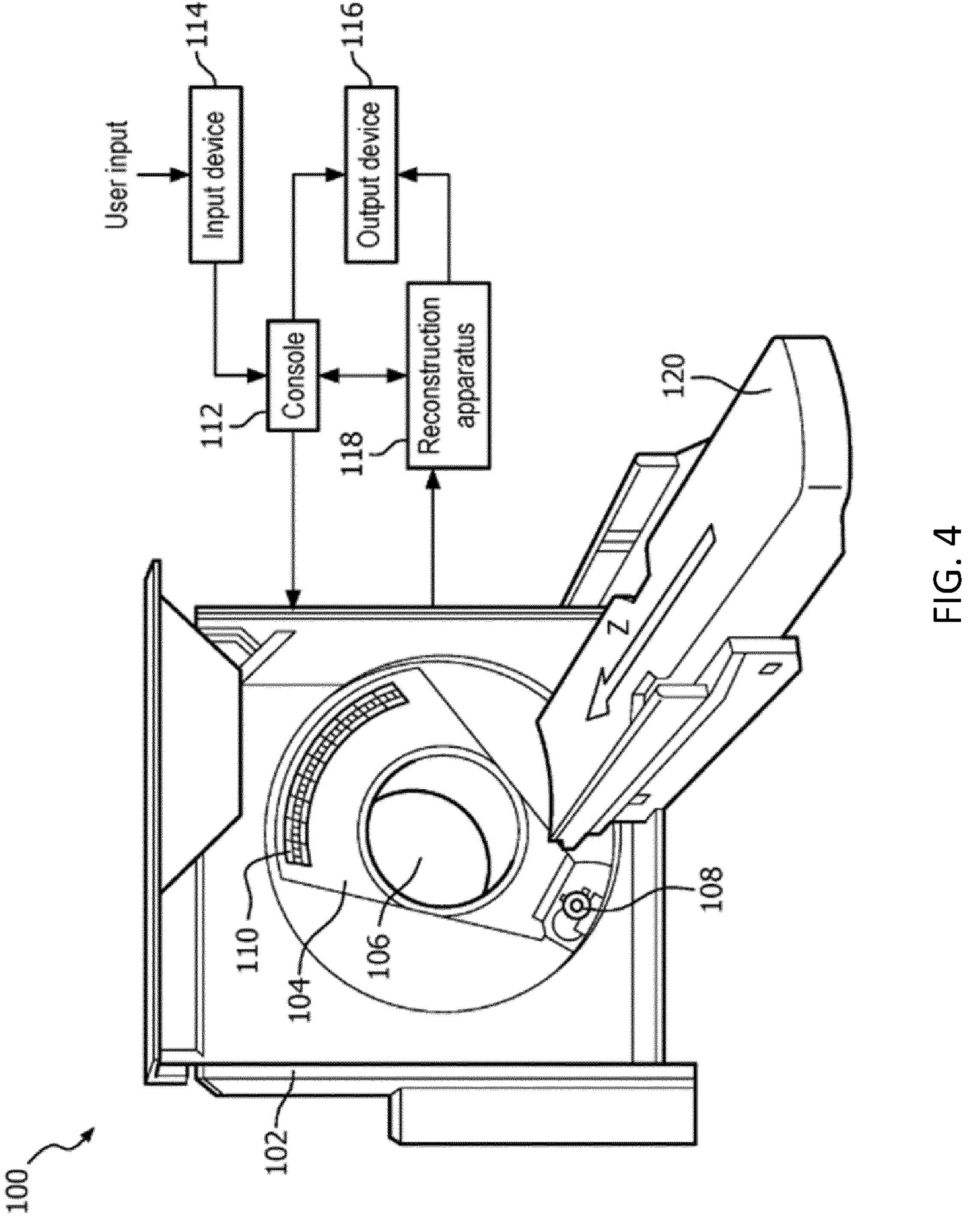
FIG. 4 schematically illustrates an example CT imaging system in accordance with one or more embodiments.

To aid understanding of forthcoming description, FIG. 4 illustrates a computed tomography (CT) imaging system 100, such as an x-ray CT scanner.

The imaging system 100 includes a generally stationary gantry 102 and a rotating gantry 104. The rotating gantry 104 is rotatably supported by the stationary gantry 102 and rotates orbitally around a longitudinal or z-axis, extending axially through an examination region 106 at a central annulus of the gantry.

A patient support 120, such as a couch, supports an object or subject such as a human patient in the examination region. The support 120 is configured to move the object or subject for loading, scanning, and/or unloading the object or subject.

A radiation source or generator 108, such as an x-ray tube, is rotatably supported by the rotating gantry 104. The radiation generator 108 rotates with the rotating gantry 104 and emits radiation that traverses the examination region 106.

A radiation sensitive detector array 110 subtends an angular arc opposite the radiation generator 108 across the examination region 106. The detector array 110 includes one or more rows of detectors that extend along the z-axis direction, detects radiation traversing the examination region 106, and generates projection data indicative thereof.

For cone-beam scanning, the radiation source generates an x-ray cone beam, and the detector array is a 2D detector array. The rotation of the radiation generator and detector around the examination region 106 (which receives a body to be scanned) may be described as orbital rotation, with the trajectory of rotation described as the orbital angular rotation axis or path.

A general-purpose computing system or computer may serve as an operator console 112 and may include an input device(s) 114 such as a mouse, a keyboard, and/or the like and an output device(s) 116 such as a display monitor, a filmer or the like. The console 112 allows an operator to control operation of the system 100.

A reconstruction apparatus 118 processes the projection data and reconstructs image data, for example volumetric image data. The data can be displayed through one or more display monitors of the output device(s) 116.

The reconstruction apparatus 118 in conventional systems may employ a filtered-backprojection (FBP) reconstruction, a (image domain and/or projection domain) reduced noise reconstruction algorithm (e.g., an iterative reconstruction) and/or other algorithm. It is to be appreciated that the reconstruction apparatus 118 can be implemented through a microprocessor(s), which executes a computer readable instruction(s) encoded or embed on computer readable storage medium such as physical memory and other non-transitory medium. Additionally or alternatively, the microprocessor(s) can execute a computer readable instruction(s) carried by a carrier wave, a signal and other transitory (or non-transitory) medium.

As noted above, one advantageous scanning protocol for cardiac imaging is the axial short scan protocol. Here, the x-ray source and detector are rotated about an arc which traverses less than a full 360 degree rotation around the subject. This is preferable for cardiac imaging since acquisition time is shorter than in a full 360 degree scan, reducing motion artifacts.

As briefly discussed above, to increase spatial resolution and sampling, the dual focal spot (DFS) acquisition approach has been developed. In dual focal spot acquisition, the location of the x-ray tube focal spot (i.e. the x-ray point source location) is alternated at high frequency between two adjacent positions throughout the orbital rotation of the CT scanner. In effect, two datasets are acquired concurrently as the x-ray scanning apparatus rotates about the 3D object, one corresponding to the first focal spot position, and one corresponding to the second focal spot position. Each focal spot forms an effective x-ray point source. The terms 'focal spot' and 'point source' may be used interchangeably in this disclosure.

Figure 5:
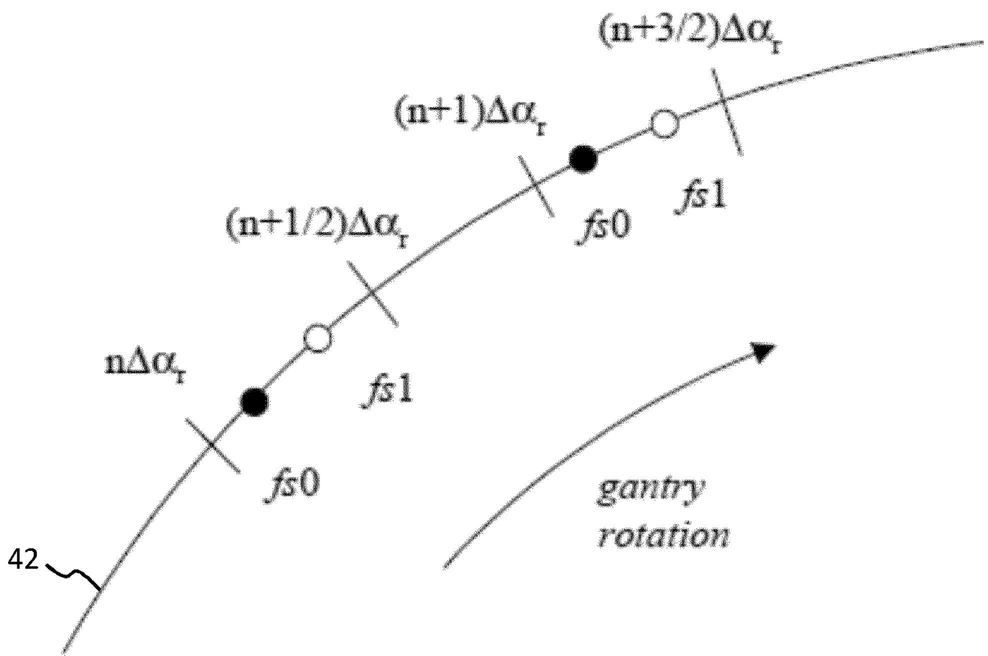
FIG. 5 schematically illustrates a dual focal spot imaging protocol according to a state-of-the-art method.

This is illustrated schematically in FIG. 5. This illustrates a portion of a rotation arc of the x-ray generator about the body being scanned. The x-ray focal spot positions, fs0, fs1 for each measured sample are shown as solid and open circles, respectively. Measurement samples for the two focal spots are acquired sequentially at each of a series of regular angular intervals, $\Delta\alpha_\tau$. In the illustrated example, the sampling period for each of fs0 and fs1 is timed such that the measurement data for both is acquired within one half of the regular angular measurement interval, $\Delta\alpha_\tau$. However this is not essential.

The two x-ray focal spots are preferably at a fixed angular distance relative to one another within the frame of reference of the x-ray generator. Since the gantry continues to move angularly throughout the data acquisition, the effective angular separation of the x-ray sources formed by the two focal points within the projection dataset is larger than the static separation between them.

There are different ways to create the alternating x-ray point sources. Both may be provided by a single x-ray tube having a pair of filaments. Alternatively, they may be provided by a radiation source having a pair of x-ray tubes, each tube including a distinct point source of radiation. Preferably, however, they may be provided by deflection means, e.g. electrostatic or electromagnetic, for deflecting an electron beam between at least two distinct focal spots on a target electrode.

Figure 6:
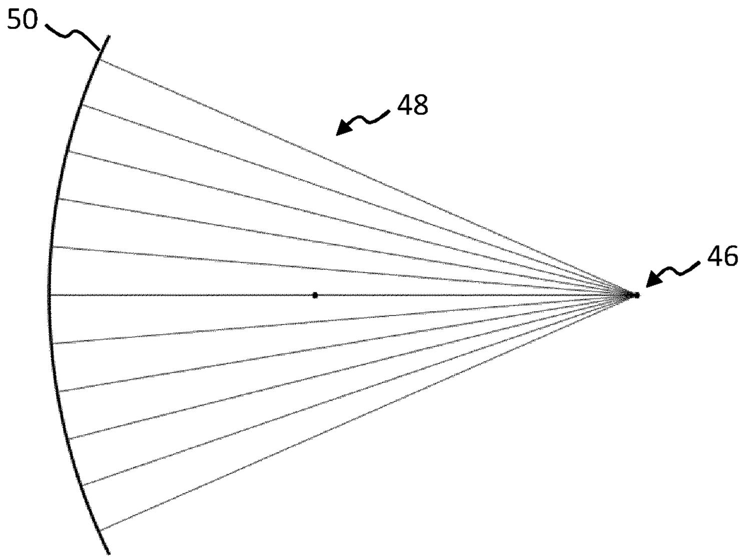
FIG. 6 schematically illustrates a fan of x-ray beams generated by a single x-ray focal spot source (single x-ray point source), in accordance with a state-of-the-art CT scanning method.

The fan of x-ray beams 48 produced by a single focal spot 46 is shown schematically in FIG. 6, where the plane of the 2D detector is illustrated by arc 50.

Figure 7:
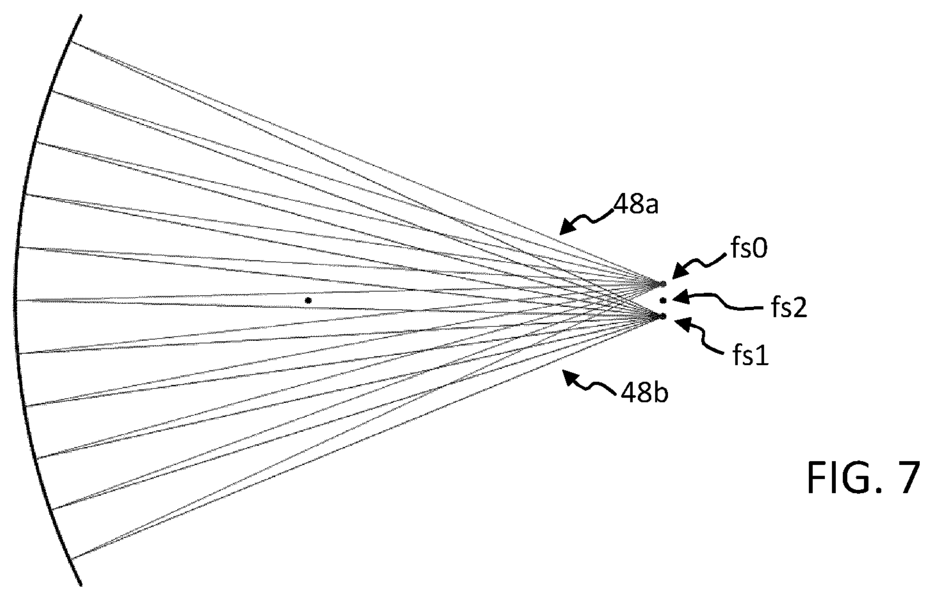
FIG. 7 schematically illustrates a fan of x-ray beams generated in accordance with a dual focal spot CT scanning operation.

By way of comparison, FIG. 7 schematically illustrates the respective fans of x-ray beams 48*a*, 48*b* produced by each of a pair of focal spots fs0, fs1 respectively.

Embodiments of the present invention are based on performing a transformation of the measurement data for the first and second focal spots into a single combined measurement dataset which represents effective measurement data for a set of effective x-ray source points located between each neighboring pair of true source points. In other words, the data are re-sampled to a new common set of effective angular x-ray source points (or sampling points). This process is known as rebinning or resampling. However, in known reconstruction operations, rebinning is done in order to map acquired data to a constructed set of sampling points which represent effective parallel source rays (parallel rebinning) However, according to embodiments of the present invention, it is proposed to re-bin the data from the two alternating source points at each of the series of orbital rotational positions into a single common angular grid of effective source points at a series of orbital rotational positions.

Figure 8:
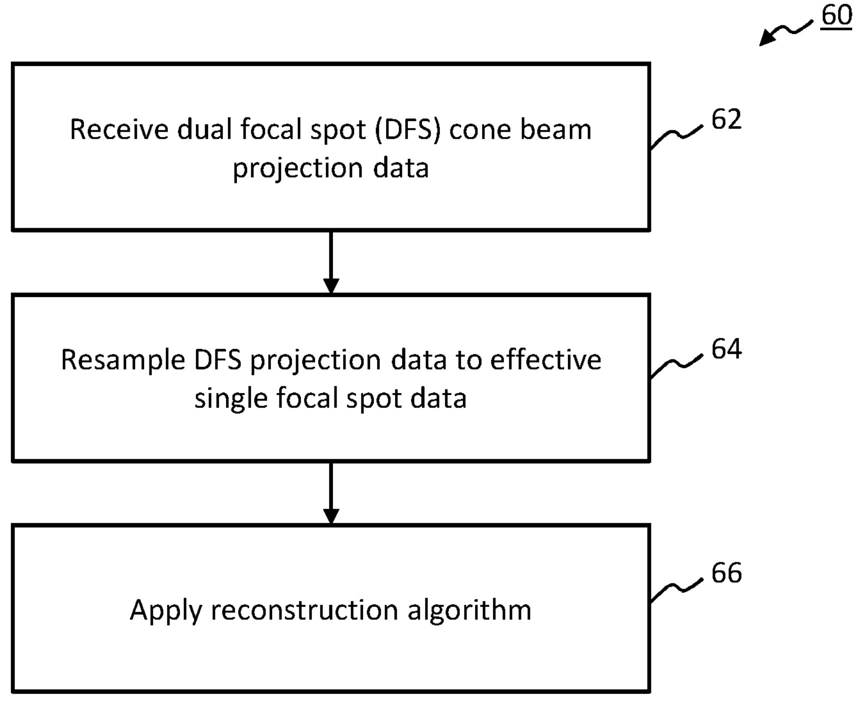
FIG. 8 outlines steps of an example method in accordance with one or more embodiments of the present invention.

FIG. 8 outlines in block diagram form the steps of an example method in accordance with one or more embodiments of the present invention. The method is for use in reconstruction of cone beam x-ray computed tomography (CT) projection data.

The method comprises receiving 62 input cone beam CT projection data of a body, wherein the CT projection data comprises at least first and second x-ray detector measurement data, corresponding to measurement data acquired with an x-ray generator providing alternately activated first and second x-ray point sources displaced relative to one another along an orbital rotational axis of the generator about the body, and the x-ray sources generating respective x-ray cone beams, and wherein each of the first and second measurement data comprises measurement data for a series of orbital rotational positions of the generator about the body.

The method further comprises processing 64 the first and second measurement data with a re-sampling operation to derive a third set of virtual measurement data for a single virtual x-ray point source, located part way between the first and second source, the third set of measurement data based on a combination of the first and second measurement data.

The method further comprises applying 66 a reconstruction algorithm to the third set of measurement data. In certain examples, the reconstruction algorithm may include a data redundancy compensation operation applied to the third set of measurement data. The data redundancy compensation operation may be a predetermined operation or may be determined or configured in real time during execution of the reconstruction algorithm.

Figure 9:
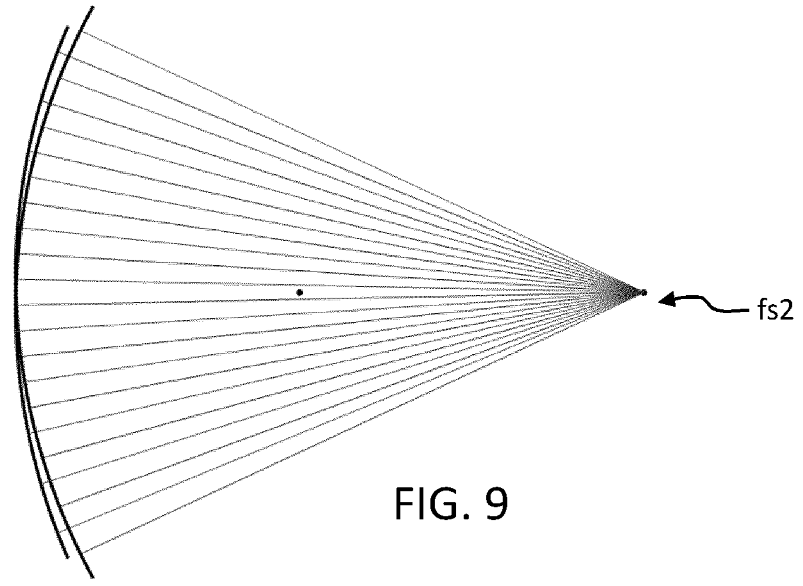
FIG. 9 schematically illustrates a resulting effective fan of x-ray beams for the virtual single x-ray point source (single x-ray focal spot) after processing of the x-ray measurement data for alternating first and second x-ray sources.
Figure 10:
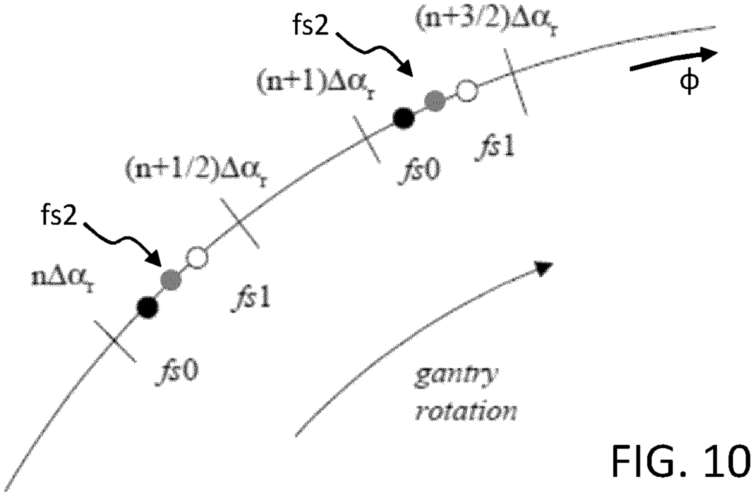
FIG. 10 schematically illustrates virtual single x-ray point sources, interpolated from an original first and second point source at different orbital rotational positions.

FIGS. 9 and 10 schematically illustrate the resampling of the data to derive the third measurement dataset. FIG. 9 schematically illustrates the virtual fan of x-ray beams projected from the virtual intermediate x-ray source point fs2 constructed via the transformation of the measurement data from the first and second x-ray source points. The resulting beam fan is effectively equivalent to a mutual rotation of each the fans 48*a*, 48*b* (see FIG. 7) about an isometric center of the fans, so as to bring each focal point fs0, fs1 to coincidence with the virtual focal spot location fs2. The resulting third measurement dataset (for the virtual source point fs2) has double the number of effective detector sampling points, i.e. double the sampling resolution, compared to each of the first and second measurement data alone (for the first and second x-ray source points respectively). The third set of measurement data represents measurement data for a virtual single cone beam propagated from the virtual focal spot location fs2. This virtual cone beam effectively comprises an interleaving of the first and second cone beam projections, and so that the third set of measurement data comprises, for each orbital angular sampling position of the single virtual point source, fs2, twice the number of detector angular sampling bins as for each of the first and second sets of measurement data.

FIG. 10 further illustrates the interpolation process for deriving the third measurement data set. FIG. 10 schematically illustrates the x-ray source point orbital angular positions as the gantry rotates orbitally. The locations of the x-ray source points fs0 and fs1 are shown as solid (black) and white circles, respectively. Projection data from each focal spot are interpolated by angular interpolation to a virtual projection dataset corresponding to a source location fs2 (shows as a grey circle).

In principle, the angular resampling can be performed to any angular grid. In the particular example of FIG. 9 and FIG. 10, the new, virtual x-ray source locations fs2 are chosen to be at each mid-point between fs0 and fs1, along the orbital angular axis, $\phi$. Use of the midpoint for the interpolation may be preferred for two main reasons. First, the distance to the nearest sample of each originally measured sample is the same. Thus, the interpolation weights used to resample data from focal spot position fs0 and from focal spot position fs1 are the same. Consequently, the interpolation induced smoothing is the same for both fs0 and fs1, which minimizes the risk of creating artefacts. Second, the distance to the nearest measured angular sample is kept small, and thus the angular smoothing introduced by the interpolation is minimized.

By way of further explanation, with reference to FIG. 10, the angular spacing between subsequent focal spot positions of each first and second focal spot is represented as $2\Delta\alpha_\tau$. To assist further explanation, the angular distance between fs0 and fs1 may be defined as $\Delta\beta$. Without loss of generality, it may be assumed that $\Delta\beta<\Delta\alpha_\tau$. Thus, there are angular sampling points for fs0 at angles $\phi_0+n\Delta\alpha_\tau$ and for fs1 at angles $\phi_0+\Delta\beta+n\Delta\alpha_\tau$ for integer n. As discussed above, the aim is to resample these data to a common angular sampling grid. By way of example, the common angular sampling grid may be chosen as $\phi_0+0.5\Delta\beta+n\Delta\alpha_\tau$ for integer n. This represents an angular sampling grid consisting of a set of new virtual single point source locations each being at a mid-point between the first and second x-ray point source locations, fs0 and fs1, along the orbital rotational axis. If the mid-point is not desired, the coefficient 0.5 can simply be replaced with any desired coefficient $\mu$ having a value between 0 and 1 to achieve a different desired interpolation point.

In this resampling step, detector values are interpolated independently for each detector pixel between adjacent angular positions. For instance, in order to resample data from the first focal spot position to a desired angular position $\phi_0+0.5\Delta\beta+i\Delta\alpha_\tau$, interpolation will be performed between measurement data acquired at $\phi_0+i\Delta\alpha_\tau$ and $\phi_0+(i+1)\Delta\alpha_\tau$. Correspondingly, in order to resample data from the second focal spot, interpolation is performed between measurement data acquired at $\phi_0+\Delta\beta+(i-1)\Delta\alpha_\tau$ and $\phi_0+\Delta\beta+i\Delta\alpha_\tau$.

Note that angular interpolation means that interpolation is done independently for each detector pixel.

It is well-known that interpolation often introduces smoothing. Smoothing implies that fine details in the final image obtained by the reconstruction process will be less visible or may even become invisible. Thus, it is preferable to minimize any smoothing during reconstruction.

The resolution loss caused by interpolation is often described by the spectrum of the so-called interpolation kernel. In this approach, interpolation is described by a convolution of the discrete samples at hand with an interpolation kernel followed by sampling at the new desired sampling points. For instance, nearest neighbor interpolation corresponds to a box-shape kernel with the width of the sampling distance of the input signal and linear interpolation corresponding to a tri-angular shaped interpolation kernel with full-width-at-half-maximum being equal to the sampling distance of the input signal.

Usually, interpolation kernels with a small support drop off more quickly in frequency space than large interpolation kernels, which implies that small interpolation kernels introduce smoothing. However, this is only true in the "average" case if an average position of the resampled data is considered. If the target sampling points are close to the original sampling points, this principle does not necessarily hold. By way of example, this can be easily seen for the extreme case in which the target sampling points coincide with the original sampling points: In this case, nearest neighbor and linear interpolation result in the same interpolated values and neither interpolation scheme introduces any smoothing. However, taking the alternate extreme case, if target sampling points are always half way between the original sampling points, then the smoothing impact of e.g. linear interpolation, is theoretically strongest since linear interpolation, in effect, represents simply an averaging of neighboring samples.

Nonetheless, although it is preferable to minimize the effect of smoothing implied by resampling, it is also a desired aim to minimize the size of the interpolation kernel in order to minimize the computational effort required for interpolation. Thus, in the context of embodiments of the present invention, it is preferable to select the target sampling points as close as possible to the original sampling points. Since it is also desired to match resolution of the resampled data from fs0 and fs1, an optimum choice is to select the new sample points (i.e. the new virtual source locations) half way between the original samples, as illustrated in FIG. 10.

Figure 11:
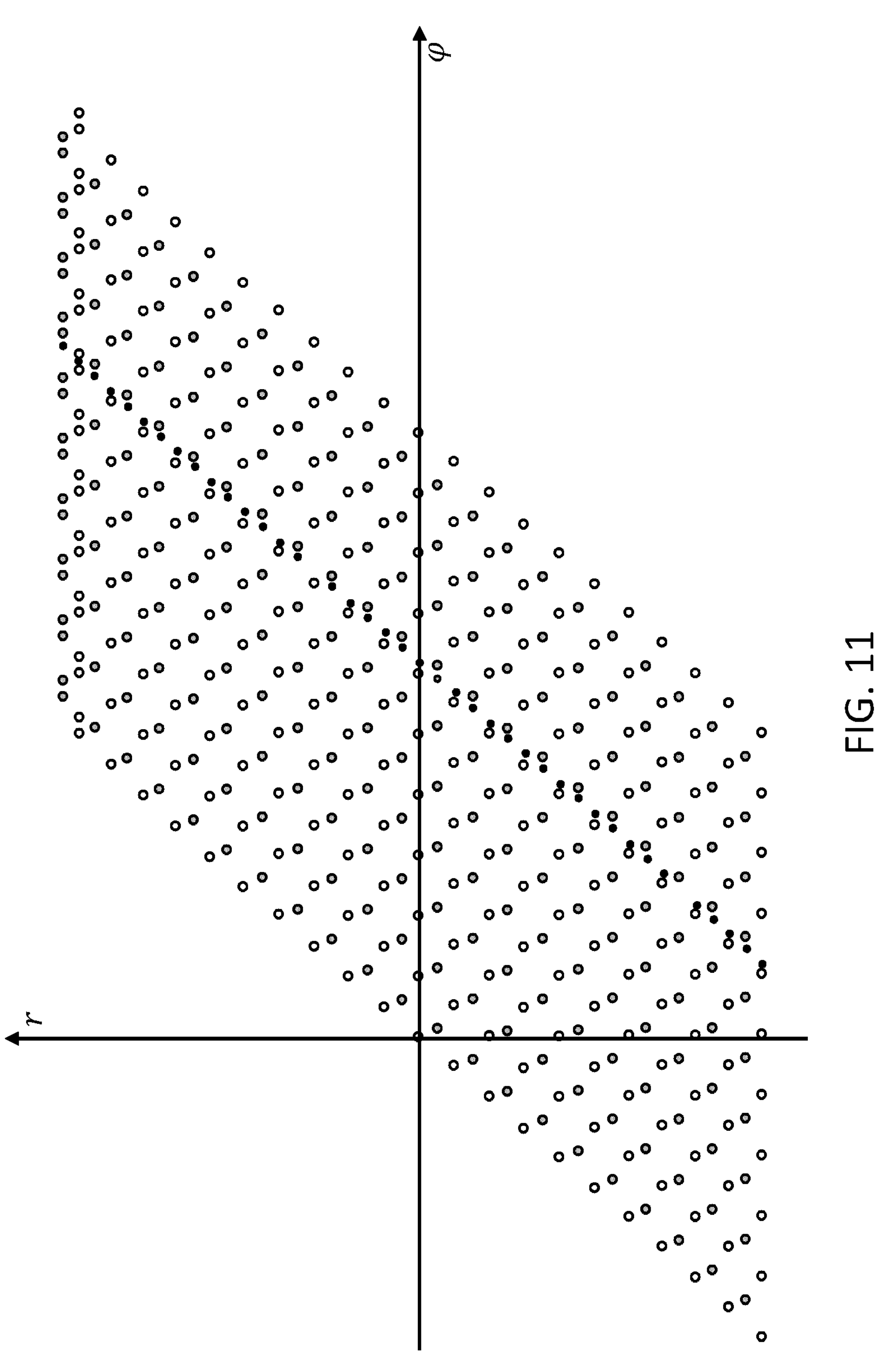
FIGS. 11 and 12 schematically depict x-ray sample points in the (r,φ) plane, and example interpolated common sampling points.
Figure 14:
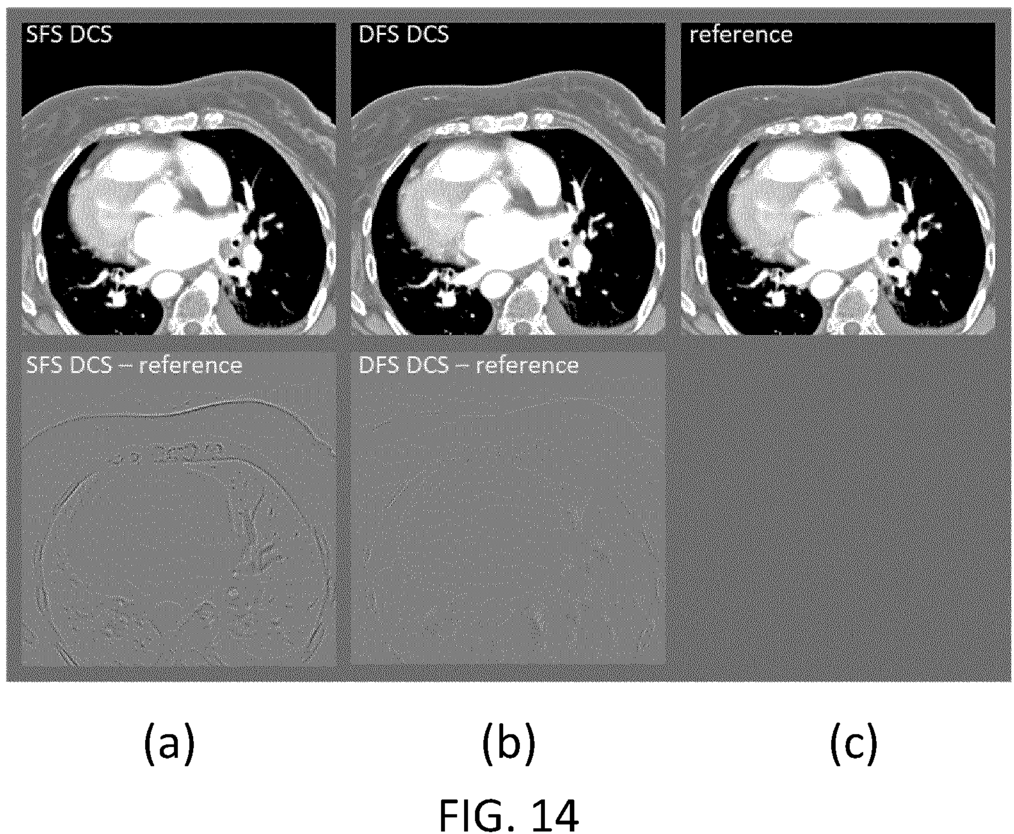
FIGS. 14 and 15 show comparative image reconstruction results for a method according to an embodiment of the present invention and for alternative state of the art methods.

By way of further explanation, FIG. 11 schematically illustrates the interpolation process in graphical form. Each ray emitted by the x-ray generator over the course of a scan is represented as a circle on the depicted graph. The imaging system can be represented by a cylindrical co-ordinate system, [z, r, φ], where φ is the orbital angle of the generator around the scanning region in the middle of the rotating gantry, containing the subject, r is the distance to the center of the scanning region, and z is the axial dimension through the scanning region. Each ray can by described by its angle φ with respect to the z-axis and its (signed) distance r to the origin (if the angle is limited to 180°). Thus, each measured sample can be represented a point in the (r, φ) plane. Sample points for fs0 and fs1 are shown in FIG. 14 as grey circles and white circles respectively. Additionally, the desired (interpolated) samples for fs2 are show as black dots.

Figure 12:
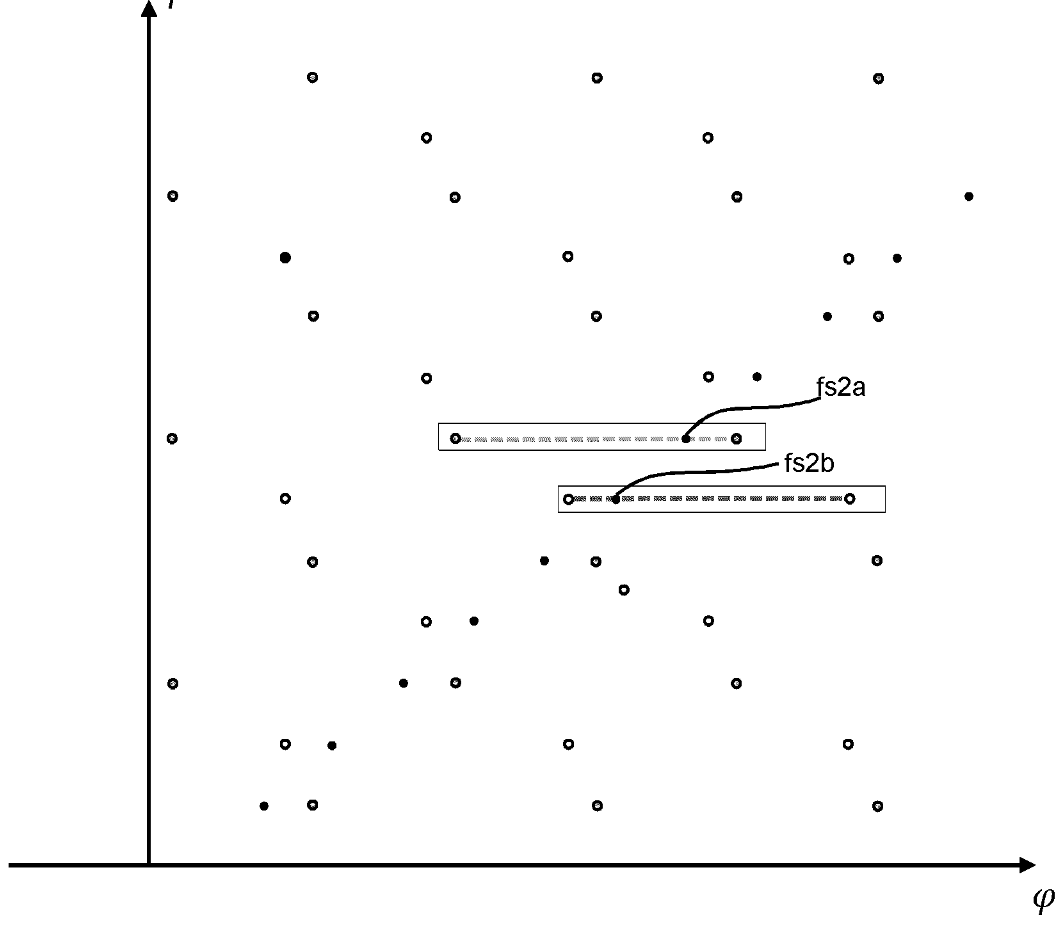

FIG. 12 shows a zoomed view of a region of FIG. 11. During angular interpolation, interpolation takes place between samples having the same r-coordinate. For example, the sample point fs2a illustrated in FIG. 12 is interpolated using only data from fs0 (closest grey points—see light grey dashed line) while sample point fs2b is interpolated using only data from fs1 (closest white points, see dark grey dashed line).

After generating the third measurement dataset for the virtual single focal spot fs2, the method further comprises applying a reconstruction algorithm.

Optionally, the reconstruction algorithm may include a determined data redundancy compensation operation applied to the third set of measurement data.

The reconstruction algorithm may be a reconstruction algorithm which does not perform parallel or wedge rebinning of data. The reconstruction algorithm may be an algorithm which performs no rebinning. The reconstruction algorithm may be an algorithm which processes the projection data in the cone-beam geometry, i.e. which retains the data in the cone beam geometry throughout the reconstruction algorithm. Embodiments of the invention find particularly advantageous application for such reconstruction algorithms, since these algorithms, by not rebinning data in these ways, do not themselves inherently perform any interleaving or amalgamation of the acquired data to a common set of angular sampling points.

As discussed above, one preferred redundancy weighting and reconstruction method is that described by Defrise and Clack in the paper: Defrise and Clack, IEEE Transaction on Medical Imaging, 13(1), 1994. This is known as the Defrise and Clack method.

This method was further developed by Schomberg in the paper: H. Schomberg, Proceedings of the Fully 3D conference 2005, Salt Lake City, page 184. This is known as the Defrise-Clack-Schomberg (DCS) method.

Another example reconstruction algorithm which follows the same principles is also detailed in the following paper by Kudo and Saito: “Derivation and implementation of a cone-beam reconstruction algorithm for nonplanar orbits”, IEEE Trans Med Imaging, 1994; 13(1):196-211.

Each of these reconstruction algorithms incorporate data redundancy compensation operations involving redundancy weighting. Any one of these methods may be applied to the derived third measurement data set according to embodiments of the invention to obtain reconstructed image data, Although these methods are mentioned specifically, more generally, any cone beam reconstruction technique can be applied to the third measurement data. One of the advantages of embodiments of the present invention is that the resampling operation described above leaves the resulting transformed projection data in a form that is suitable for application of almost any reconstruction technique known in the art.

Figures 13A, 13B:
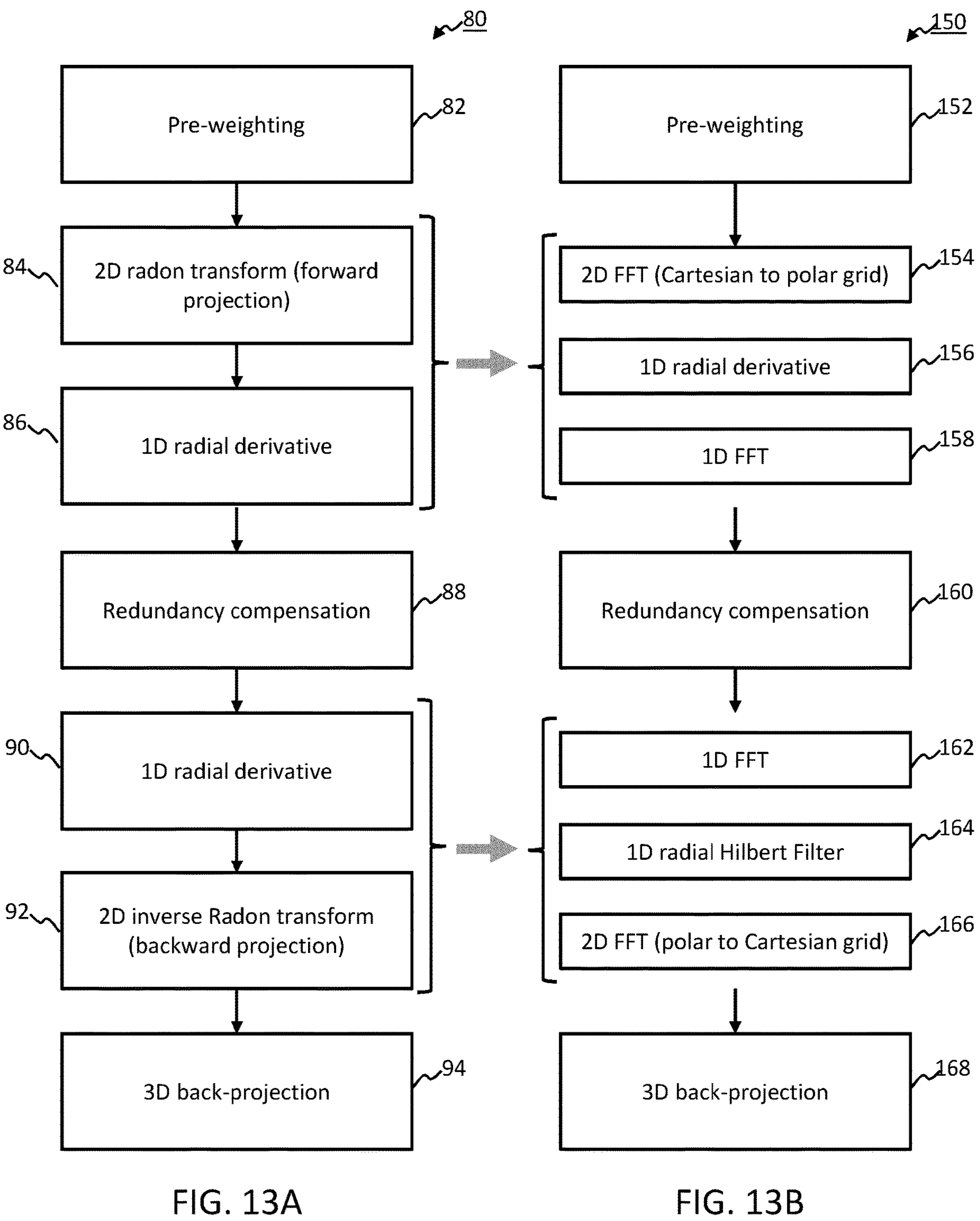
FIGS. 13A and 13B outline steps of two example image reconstruction algorithms, suitable for application following generation of third measurement data based on original first and second measurement data.

With regards to the Defrise and Clack reconstruction method, the steps of this method are outlined in summary form in FIG. 13A. FIG. 13B outlines in summary form the steps of the Defrise-Clack-Schomberg (DCS) method. The relationship between the Defrise and Clack and the DFS method is schematically indicated by the grey arrows between FIG. 13A and FIG. 13B. In each case, the input to the respective reconstruction algorithm is the third measurement data (third projection data), derived through the above-described processing of the first and second measurement data. Full details of each of the steps outlined below can be found in the relevant papers cited above.

With regards first to the Defrise and Clack method, the steps of the method comprise first performing a pre-weighting 82 of the input projection data.

The method further comprises applying a 2D radon transform 84 to the pre-weighted data.

The method further comprises applying a 1D radial derivative 86 following the radon transform. As discussed above with reference to FIG. 11 and FIG. 12, a ray from the x-ray generator may be parametrized by polar coordinates r and φ. In the present context, φ has values from 0 to 360° and r from 0 to infinity Radial filtering means filtering along samples with the same value of φ.

Following the 1D radial derivative, a redundancy compensation operation 88 is performed which comprises applying weightings to the measurement data from the different orbital angular positions of the detector relative to the subject.

Following the redundancy compensation, a 1D radial derivative 90 is again applied, followed by a 2D inverse radon transform 92 (backward projection). This is followed by a 3D back-projection 94 to arrive at reconstructed image data.

The steps of the DCS method are outlined in FIG. 13B. The steps are similar to those of the Defrise and Clack method of FIG. 13A, except that the steps of the 2D radon transform and the 1D radial derivative are slightly modified.

The DFS method begins with a pre-weighting step 152 applied to the input projection data (the third measurement data). This step is similar to that of the Defrise-Clack method above. This is followed by a 2D Fast Fourier Transform (FFT) 154 which is applied to transform the co-ordinate system from Cartesian co-ordinates to polar co-ordinates. This is followed by a 1D radial derivative 156. This is followed by a 1D FFT 158.

The method next comprises a redundancy compensation operation 160. This can be similar to the operation performed in the Defrise and Clack method and described above.

Following the redundancy compensation operation, the method comprises a 1D FFT 162.

This is followed by application of a 1D radial Hilbert filter 164.

This is followed by a 2D FFT 166 to achieve a co-ordinate system transformation from polar back to Cartesian co-ordinates.

A 3D back-projection 168 is then applied resulting in reconstructed image data.

Figure 15:
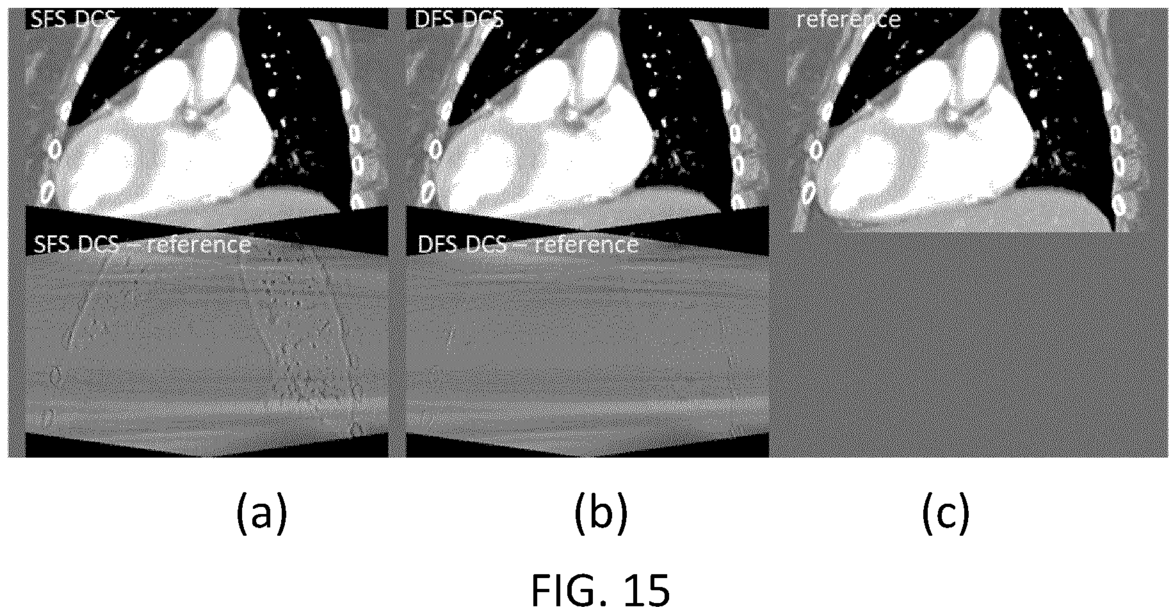

Results of application of the method according to one or more embodiments of the present invention are illustrated in FIG. 14 and FIG. 15. FIGS. 14(*a*) and 15(*a*) show reconstruction results for application of a single focal spot (SFS) CT scanning method, and application of the DCS reconstruction algorithm. FIGS. 14(*b*) and 15(*b*) show reconstruction results for a method in accordance with embodiments of the present invention, comprising application of the dual focal spot (DFS) CT scanning method outlined above, and application of the DCS reconstruction algorithm. FIGS. 14(*c*) and 15(*c*) each show a reference reconstruction result derived using a narrow collimation and wedge reconstruction.

As can be seen from the different results, the SFS-DCS image in each case (FIG. 14(*a*), 15(*a*)) has a lower spatial resolution than the reference reconstruction (FIG. 14(*c*), 15(*c*)), whereas the DFS-DCS reconstruction in each case (FIG. 14(*b*), 15(*b*)) provides an improved resolution compared to the reference reconstruction (FIG. 14(*c*), 15(*c*)).

No artefacts are introduced by the additional interpolation performed as part of the method of embodiments of the present invention.

Examples in accordance with a further aspect the invention provide a computer program product comprising code means configured, when executed on a processor, to cause the processor to perform a method in accordance with any example or embodiment outlined above or described below, or in accordance with any claim of the present application.

Examples in accordance with a further aspect invention provide a processing arrangement for use in reconstruction of cone beam x-ray computed tomography (CT) projection data. A processing arrangement comprises an input/output; and one or more processors operatively coupled with the input/output. The more processors are adapted to perform the following steps:

- receive, at the input/output, input cone beam CT projection data of a body, wherein the CT projection data comprises at least first and second x-ray detector measurement data, corresponding to measurement data acquired with an x-ray generator providing alternately activated first and second x-ray point sources displaced relative to one another along an orbital rotational axis of the generator about the body, and the x-ray sources generating respective x-ray cone beams, and wherein each of the first and second measurement data comprises measurement data for a series of orbital rotational positions of the generator about the body;
- process the first and second measurement data with a re-sampling operation to derive a third set of measurement data corresponding to a virtual single x-ray point source located part way between the first and second x-ray point sources, the third set of measurement data based on a combination of the first and second measurement data; and
- apply a reconstruction algorithm to the third set of measurement data.

Examples in accordance with a further aspect the invention also provide an x-ray computed tomography (CT) imaging system. The system comprises an x-ray CT imaging apparatus, comprising an x-ray generator and an x-ray detector, the x-ray detector and x-ray generator mounted on a rotatable gantry permitting orbital angular rotation of the detector and generator around the examination region. The x-ray generator is adapted in use to alternately activate first and second x-ray point sources displaced relative to one another along the orbital rotational axis, and the first and second x-ray sources generating respective x-ray cone beams, The x-ray detector comprises a 2D detector array.

The system further comprises a processing module adapted to perform the following steps:

- obtain from the x-ray detector first and second x-ray detector measurement data, corresponding to measurement data acquired with the alternately activated first and second x-ray point sources, and the first and second measurement data each comprising measurement data for a series of orbital rotational positions about the body;
- process the first and second measurement data with a re-sampling operation to derive a third set of measurement data corresponding to a virtual single x-ray point source located part way between the first and second x-ray point sources, the third set of measurement data based on a combination of the first and second measurement data; and
- apply a reconstruction algorithm to the third set of measurement data. Optionally, the reconstruction algorithm may include a data redundancy compensation operation applied to the third set of measurement data. This may be a pre-determined operation, or it may be determined in real time during execution of the reconstruction algorithm.

By way of example, one example CT imaging apparatus suitable for use in accordance with embodiments of the present invention has been described in detail above with reference to FIG. 4. In accordance with examples, the processing module of the CT imaging system above may be implemented by the reconstruction apparatus 118 of the example system outlined in FIG. 4.

Embodiments of the invention described above employ a processing arrangement. The processing arrangement may in general comprise a single processor or a plurality of processors. It may be located in a single containing device, structure or unit, or it may be distributed between a plurality of different devices, structures or units. Reference therefore to the processing arrangement being adapted or configured to perform a particular step or task may correspond to that step or task being performed by any one or more of a plurality of processing components, either alone or in combination. The skilled person will understand how such a distributed processing arrangement can be implemented. The processing arrangement includes a communication module or input/output for receiving data and outputting data to further components.

The one or more processors of the processing arrangement can be implemented in numerous ways, with software and/or hardware, to perform the various functions required. A processor typically employs one or more microprocessors that may be programmed using software (e.g., microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

A single processor or other unit may fulfill the functions of several items recited in the claims.

The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

If the term "adapted to" is used in the claims or description, it is noted the term "adapted to" is intended to be equivalent to the term "configured to". Any reference signs in the claims should not be construed as limiting the scope.

The invention claimed is:

1. A method for reconstructing computed tomography (CT) projection data, comprising:

receiving the CT projection data of a body, wherein the CT projection data comprises at least first and second x-ray detector measurement data corresponding to measurement data acquired with an x-ray generator providing alternately activated first and second x-ray point sources displaced relative to one another along an orbital rotational axis of the x-ray generator about the body, the x-ray sources generating respective x-ray cone beams, and wherein each of the first and second measurement data comprises measurement data for a series of orbital rotational positions of the generator about the body;

processing the first and second measurement data with a re-sampling operation comprising angular interpolation along the orbital rotational axis about the body to derive a third set of measurement data representing projection data of a single virtual cone beam propagated from a virtual single x-ray point source located at a mid-point between the first and second x-ray point source locations, along the orbital rotational axis, the virtual single x-ray point source having a plurality of orbital angular sampling positions about the body, and the third set of measurement data being based on the first and second measurement data; and applying a reconstruction algorithm to the third set of measurement data.

2. The method as claimed in claim 1, wherein the reconstruction algorithm includes a data redundancy compensation operation applied to the third set of measurement data.

3. The method as claimed in claim 1, wherein deriving the third set of measurement data is based on interpolation between the first and second measurement data.

4. The method as claimed in claim 3, wherein the interpolation is angular interpolation along a direction of the orbital rotational axis about the body.

5. The method as claimed in claim 1, wherein the third set of measurement data comprises, for each orbital angular sampling position of the virtual single x-ray point source, twice the number of detector angular sampling bins as for each of the first and second sets of measurement data.

6. The method as claimed in claim 1, wherein the projection data of the virtual single x-ray point source comprises an interleaving of the projection data of the first and second cone beams.

7. The method of claim 6, wherein the re-sampling comprises a rotation of each of the first and second cone beams about an isocenter of the orbital rotation such that the point sources coincide at the single virtual point source location.

8. An x-ray computed tomography (CT) imaging system, comprising:

an x-ray CT imaging apparatus comprising an x-ray generator and an x-ray detector, the x-ray detector and x-ray generator mounted on a rotatable gantry permitting orbital angular rotation of the detector and generator around an examination region, wherein the x-ray generator is configured to alternately activate first and second x-ray point sources displaced relative to one another along an orbital rotational axis, and the first and second x-ray sources generating respective x-ray cone beams, wherein the x-ray detector comprises a 2D detector array; and at least one processor configured to:

obtain from the x-ray detector first and second x-ray detector measurement data corresponding to respective measurement data acquired with the alternately activated first and second x-ray point sources, the first and second measurement data each comprising measurement data for a series of orbital rotational positions of the x-ray generator about the body, process the first and second measurement data with a re-sampling operation comprising angular interpolation along the orbital rotational axis about the body to derive a third set of measurement data representing projection data for a single virtual cone beam propagated from a virtual single x-ray point source located at a mid-point between the first and second x-ray point source locations, along the orbital rotational axis, the single point source having a plurality of orbital angular sampling positions about the body, the third set of measurement data based on a combination of the first and second measurement data, and apply a reconstruction algorithm to the third set of measurement data.

9. The system as claimed in claim 8, wherein deriving the third set of measurement data is based on interpolation between the first and second measurement data.

10. A non-transitory computer-readable medium for storing executable instructions, which cause a method to be performed to reconstruct computed tomography (CT) projection data, the method comprising:

receiving the CT projection data of a body, wherein the CT projection data comprises at least first and second x-ray detector measurement data corresponding to measurement data acquired with an x-ray generator providing alternately activated first and second x-ray point sources displaced relative to one another along an orbital rotational axis of the x-ray generator about the body, the x-ray sources generating respective x-ray cone beams, and wherein each of the first and second measurement data comprises measurement data for a series of orbital rotational positions of the generator about the body;

processing the first and second measurement data with a re-sampling operation comprising angular interpolation along the orbital rotational axis about the body to derive a third set of measurement data representing projection data of a single virtual cone beam propagated from a virtual single x-ray point source located at a mid-point between the first and second x-ray point source locations, along the orbital rotational axis, the virtual single x-ray point source having a plurality of orbital angular sampling positions about the body, and the third set of measurement data being based on the first and second measurement data; and applying a reconstruction algorithm to the third set of measurement data.

* * * * *